United States Patent
Pei et al.

(10) Patent No.: US 9,782,443 B2
(45) Date of Patent: Oct. 10, 2017

(54) PREPARING TOOTH-LIKE STRUCTURE USING STEM CELL

(71) Applicant: GUANGZHOU INSTITUTES OF BIOMEDICINE AND HEALTH, CHINESE ACADEMY OF SCIENCES, Guangzhou (CN)

(72) Inventors: Duanqing Pei, Guangzhou (CN); Jinglei Cai, Guangzhou (CN); Pengfei Liu, Guangzhou (CN); Shubin Chen, Guangzhou (CN); Yanmei Zhang, Guangzhou (CN)

(73) Assignee: Guangzhou Institutes Of Biomedicine And Health, Chinese Academy Of Sciences, Guangzhou (CN)

(*) Notice: Subject to any disclaimer, the term of this patent is extended or adjusted under 35 U.S.C. 154(b) by 0 days.

(21) Appl. No.: 14/765,949

(22) PCT Filed: Feb. 5, 2013

(86) PCT No.: PCT/CN2013/071408
§ 371 (c)(1),
(2) Date: Aug. 5, 2015

(87) PCT Pub. No.: WO2014/121449
PCT Pub. Date: Aug. 14, 2014

(65) Prior Publication Data
US 2016/0000836 A1 Jan. 7, 2016

(51) Int. Cl.
*A61K 35/22* (2015.01)
*C12N 5/074* (2010.01)
*A61K 35/545* (2015.01)
*C07K 14/51* (2006.01)
*C12N 5/077* (2010.01)

(52) U.S. Cl.
CPC ............ *A61K 35/545* (2013.01); *C07K 14/51* (2013.01); *C12N 5/0654* (2013.01); *C12N 2500/33* (2013.01); *C12N 2500/38* (2013.01); *C12N 2501/06* (2013.01); *C12N 2501/155* (2013.01); *C12N 2501/385* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 8,129,187 B2 * | 3/2012 | Yamanaka | C07K 14/4702 435/375 |
| 2006/0051860 A1 * | 3/2006 | Ishikawa | A61L 27/3834 435/325 |
| 2010/0119997 A1 * | 5/2010 | Tsuji | C12N 5/0654 433/215 |

FOREIGN PATENT DOCUMENTS

| CN | 1615149 A | 5/2005 |
|---|---|---|
| CN | 1738654 A | 2/2006 |

OTHER PUBLICATIONS

Wen et al., Application of Induced Pluripotent Stem Cells in Generation of a Tissue-Engineered Tooth-Like Structure. Tissue Engineering: Part A vol. 18, Nos. 15 and 16, 2012. p. 1677-1686.*
Metallo et al., Retinoic Acid and Bone Morphogenetic Protein Signaling Synergize to Efficiently Direct Epithelial Differentiation of Human Embryonic Stem Cells. Stem Cells 2008;26:372-380.*
Ning et al., Differentiation of mouse embryonic stem cells into dental epithelial-like cells induced by ameloblasts serum-free conditioned medium. Biochemical and Biophysical Research Communications 394 (2010) 342-347.*
Akopian et al., Comparison of defined culture systems for feeder cell free propagation of human embryonic stem cells. In Vitro Cell.Dev.Biol.—Animal (2010) 46:247-258.*
Evseenko et al., Mapping the first stages of mesoderm commitment during differentiation of human embryonic stem cells. PNAS, 2010, 107:13742-13747.*
Wang et al., Induced pluripotent stemcell lines derived from human gingival fibroblasts and periodontal ligament fibroblasts. J Periodont Res 2011; 46: 438-447.*
Cai et al., Generation of tooth-like structures from integration-free human urine induced pluripotent stem cells. Cell Regeneration 2013, 2:1-8.*
Zhou et al., Generation of human induced pluripotent stem cells from urine samples. Nature protocols. vol. 7, No. 12, 2012. pp. 2080-2089.*
Ludwig et al., Derivation of human embryonic stem cells in defined conditions. Nature Biotechnology vol. 24 No. 2 Feb. 2006, 185-187.*
PCT/CN2013/071408 International Search Report and Written Opinion mailed Nov. 21, 2013, 17 pages.

* cited by examiner

*Primary Examiner* — Christopher M Babic
*Assistant Examiner* — Arthur S Leonard
(74) *Attorney, Agent, or Firm* — Lathrop & Gage LLP

(57) ABSTRACT

The usage of a stem cell in preparation of a tooth-like structure is provided. And a culture medium, a method for preparing an epithelial-like cell, a kit for preparing an ameloblast, a method for preparing an ameloblast are also provided. Specifically, the culture medium comprises a basal medium, which is DMEM/F12 medium; N2 supplement; retinoic acid; and BMP-4.

16 Claims, 3 Drawing Sheets

PREPARING TOOTH-LIKE STRUCTURE USING STEM CELL

CROSS-REFERENCE TO RELATED APPLICATION

None

FIELD

The present disclosure relates to the field of biotechnology, in particular, the present disclosure relates to the usage of a stem cell in preparation of a tooth-like structure, a culture medium, a method for preparing an epithelial-like cell, a kit for preparing an ameloblast, method for preparing an ameloblast.

BACKGROUND

The differentiated products of iPSCs (induced pluripotent stem cells) have been used successfully in animal models of diseases, injury and aging, such as Pakinson disease, beta-thalassemia, hepatic disease, and spinal cord injury.

However, no solid organs or tissues such as tooth have been generated with human iPSCs.

SUMMARY

In view thereof, the present disclosure is directed to provide the usage of a stem cell in preparation of a tooth-like structure, a culture medium, a method for preparing an epithelial-like cell, a kit for preparing an ameloblast, method for preparing an ameloblast.

In a first aspect of present disclosure, according to an embodiment of the present disclosure, the usage of a stem cell in preparation of a tooth-like structure may be provided. In one embodiment the tooth-like is produced in a mammalian animal by means of xenograft transplantation. In one embodiment the mammalian animal is at least one selected from a group consisting of mouse, rat, pig, dog, and monkey. In one embodiment the stem cell may be induced to form an epithelial-like cell prior to the xenograft transplantation. In one embodiment the stem cell is an embryo stem cell or an induced pluripotent stem cell. And in one embodiment, the induced pluripotent stem cell may be produced from a human cell, and the human cell may be at least one selected from a group consisting of urine cell, skin fibroblast, and periodontal ligament stem cell. And in one embodiment, the tooth-like structure contains ameloblast.

The term of "tooth-like structure" may be identified with histology section and stained with human specific antibodies human leukocyte antigen-I (HLA-I, 1:50, abcam, Cat. NO. ab70328) and human nucleus antigen (hNA, 1:500, Millipore, Cat. NO. 1969098) indicating the structure and derivatives of human cells in tooth-like structure. The immunohistochemistry staining with Ameloblastin (Amel, 1:100, Santa, Cat. NO. sc-50534) may be used to describe the appearance of enamel-secreting ameloblasts in the tooth-like structures, which are produced by the epithelial sheets derived from hESCs or iPSCs.

In a second aspect of present disclosure, a culture medium may be provided. According to an embodiment of the present disclosure, the culture medium may comprise: a basal medium, which is DMEM/F12 medium; a N2 supplement; a retinoic acid; and a BMP-4. And in one embodiment, the culture medium may comprise a N2 supplement of about 1 wt. %, a retinoic acid of about 1 µM, and a BMP-4 of about 25 ng/ml. The inventors surprisingly find that the above cited culture medium may be effectively used to induce the differentiation of stem cell into epithelial-like cell. And the epithelial-like cell may be further transplanted into the body of an animal, to form a tooth-like structure.

In a third aspect of present disclosure, a method for preparing an epithelial-like cell may be provided. According to an embodiment of the present disclosure, the method may comprise culturing a stem cell to induce the stem cell differentiating into the epithelial-like cell using the above described culture medium, wherein the stem cell is an embryo stem cell or an induced pluripotent stem cell. The inventors surprisingly find that method uses the above cited culture medium, and then the method may be effectively used to induce the differentiation of stem cell into epithelial-like cell. And the epithelial-like cell may be further transplanted into the body of an animal, to form a tooth-like structure. According to an embodiment of the present disclosure, the induced pluripotent stem cell is produced from a human cell. According to an embodiment of the present disclosure, the human cell is at least one selected from a group consisting of urine cell, skin fibroblast, and periodontal ligament stem cell. The person skilled in the art may obtain "Human induced pluripotent stem cells (hiPSCs)" from human urine cells by two different systems: 1) pMX-based retroviral system (Oct4, Sox2, K1f4, and c-Myc, Addgene); 2) Electroporation with oriP/EBNA episomal vectors (Oct4, Sox2 SV4OLT, K1f4 and miR302/367). The person skilled in the art may obtain "Human induced pluripotent stem cells (hiPSCs)" from human skin fibroblasts and periodontal ligament by pMX-based retroviral system (Oct4, Sox2, K1f4, and c-Myc, Addgene) (Esteban, M. A. et al., Vitamin C enhances the generation of mouse and human induced pluripotent stem cells. Cell Stem Cell. 2010: 6,71-9; Cai, J. et al. Generation of human induced pluripotent stem cells from umbilical cord matrix and amniotic membrane mesenchymal cells. J Biol Chem. 2010: 285,11227-34, which are incorporated here by reference). Under human embryo stem cells (hESCs) culture conditions, hiPSCs are very similar to hESCs in cell morphology, growth properties, surface marker expression, teratoma formation, and multi-lineage in vitro differentiation.

In one embodiment, "Human urine cells" described herein preferably are such cells which are collected from only the mid-stream of urine with 150-200 ml in the appropriate sterilized containers (up to 500 ml). In one embodiment, the human urine cell may be obtained through the following procedures. Urine samples were centrifuged at 400 g for 10 minutes at room temperature and then resuspended in PBS containing ampothericin B and penicillin/streptomycin. After washing with PBS, the cell pellet from urine sample is cultured in primary medium, containing DMEM/Ham's F12 1:1 (Hyclone), 10 wt. % of fetal bovine serum (FBS; PAA), SingleQuot Kit CC-4127 REGM (Lonza), ampothericin B and penicillin/streptomycin. The medium is kept in a small volume during the first 2 days. In the following days, the medium was changed to REBM (Renal Epithelial Basal 2 Medium, Lonza) medium containing SingleQuot Kit CC-4127 REGM (Lonza). Visible cells/colonies appeared routinely after 3-6 days, typically 3-5 per sample on average. The first full media change was made after the first cells/colonies were seen. Cells were then split onto a bigger surface aided by 0.25% trypsin containing 1 mM EDTA when the culture grew confluent. RPTECs were obtained from a biopsy and maintained in urine cell medium.

In one embodiment, "skin fibroblasts" described herein preferably are such cells which are collected from a small piece of human skin tissue. In one embodiment, the skin fibroblast may be obtained through the following procedures. The skin tissue were minced into small tissue cubes and then plated in DMEM supplemented with 10 wt. % fetal bovine serum (FBS; Hyclone), 100 units/mL penicillin streptomycin (Hyclone). The skin keratinocytes appear first surround the small pieces of skin tissues. The skin fibroblasts were then produced thereafter. The cells at passages P3-P5 may be used.

In one embodiment, "periodontal ligament stem cells" described herein preferably are such cells which are collected from human periodontal ligament (PDL) tissues separated from the mid-third of the root surface. In one embodiment, periodontal ligament stem cells may be obtained through the following procedures. PDL tissues were minced into small tissue cubes (approximately 1 mm$^3$) and digested with a solution of 3 mg/mL collagenase (type I) with 4 mg/mL dispase (both from Sigma—Aldrich, St. Louis, Mo., USA) in α-minimum essential medium (α-MEM, Hyclone, Road Logan, Utah, USA) for 15 min at 37 ° C. with vigorous shaking. The tissue explants were then plated and cultured in α-MEM supplemented with 10 wt. % fetal bovine serum (FBS; Hyclone), 0.292 mg/mL glutamine (Hyclone), 100 units/mL penicillin streptomycin (Hyclone), and 100 μm/L ascorbic acid (Sigma—Aldrich). Single cell-derived colony cultures were obtained using the limiting dilution technique and passage 0 (P0) cells were cultured. To avoid changes in cell behaviors that are associated with prolonged culture, the cells at passages P3-P5 may be used.

In one embodiment, "embryonic stem cells" described herein preferably are H1 ESC line purchased from NATIONAL STEM CELL BANK IN USA, which are maintained its pluripotency on the Matrigel-coated plates in mTesR1 medium with passages every 3-5 days.

In a forth aspect of present disclosure, a kit for preparing an ameloblast may be provided, and the kit may comprises: a first culture medium, which is the culture medium described above; a second culture medium, which is DMEM medium supplemented with FBS, non-essential amino acid, glutamine, penicillin and streptomycin, wherein the first culture medium and the second medium is provided in a different container respectively. The inventors surprisingly find that kit may be used to prepare ameloblast. According to an embodiment of the present disclosure, the kit may further comprising a third culture medium, which is at least one selected from mTeSR1™ medium, E8 medium, and KSR conditioned medium. According to an embodiment of the present disclosure, the second culture medium comprises FBS of about 10 wt. %, glutamine of about 2 mM, non-essential amino acid of about 0.1 mM, penicillin of about 100 U/ml, and streptomycin of 100 U/ml.

In one embodiment, the epithelial-like cell may form an epithelial sheet. In one embodiment, the differentiating cells can be harvested as the intact epithelial sheets at Day 7 (D7) and D14 during the differentiation. Small pieces of epithelial sheets may be obtained at D21 during the differentiation. In one embodiment, the differentiating epithelial cells from both hESCs and iPSCs may be identified with the expression of pluripotent cell marker Oct4, epithelial markers K18, p63, K19, CD29, and K14, and observed under electronic microscopes (EM).

As described in the present disclosure, the intact epithelial sheets derived from stem cells may be further induced to form tooth-like structures by recombination with dental mesenchyme.

In a fifth aspect of present disclosure, a method for preparing an ameloblast may be provided, and according to an embodiment of the present disclosure, the method may comprise preparing an epithelial-like cell by a method described above; recombining the epithelial-like cell with a dental mesenchyme of a first animal to obtain a recombinant specimen; culturing the resulting recombinant specimen to obtain a reconstituted explant; transplanting the reconstituted explant into a second animal for at a predetermined time to form the ameloblast.

FIG. 1 shows a schematic representation of procedures for tooth generation from hESCs and urine cell derived hiPSCs in one example of present disclosure. A chimeric culture system is developed for tooth regeneration from hESCs and human urine cell derived iPSCs. Briefly, referring to FIG. 1, hESCs or hiPSCs can be induced to produce epithelial sheets capable of replacing the E14.5 mouse dental epithelium in a reconstitution process. The reconstituted explants can then be cultured in vitro for 1-2 days and transplanted beneath mouse subrenal capsule for 3 weeks (≥2 weeks) for tooth regeneration (FIG. 1).

According to an embodiment of the present disclosure, the stem cell is cultured for about 5-10 days, preferably about 7 days, using the culture medium described above. According to an embodiment of the present disclosure, the first animal and the second animal are independently selected from a group consisting of mouse, rat, pig, dog, and monkey respectively. According to an embodiment of present disclosure, the second animal is preferably of immunodeficiency, which may be caused by administrating a dose of Cyclosporine A to the animal. According to an embodiment of the present disclosure, the first animal is a fetal mouse, and the second animal is a nude mouse. According to an embodiment of the present disclosure, the dental mesenchyme is mechanically separated from a tooth germ, and the tooth germ is digested using a protease prior to the separation. According to an embodiment of the present disclosure, the protease is a Dispase of about 0.75 mg/ml. According to an embodiment of the present disclosure, the resulting recombinant specimen is cultured using a DMEM medium supplemented with FBS, non-essential amino acid, glutamine, penicillin and streptomycin. According to an embodiment of the present disclosure, the recombinant tissue is transplanted into a space under a kidney capsule of the nude mouse. According to an embodiment of the present disclosure, the predetermined time is about 2 to 4 weeks. According to an embodiment of the present disclosure, the predetermined time is about 3 weeks. According to an embodiment of the present disclosure, the stem cell is cultured using at least one selected from mTeSR1™ medium, E8 medium, and KSR conditioned medium prior to preparing the epithelial-like cell, wherein the medium is replaced with the culture medium described above when the cultured stem cell reach a confluence of about 60-80%, to obtain the epithelial-like cell. It is surprisingly found by the inventors that the above described method may be effectively used to produce an ameloblast. And the ameloblast may be contained in a tooth-like structure. With the histology examination, followed by decalcification, the inventors find that the tooth-like structure contains dental pulp, dentin, enamel space, and enamel organ. And with Raman spectroscopy and Nano-indentation method, the inventors find that the tooth-like structure have the similar compositions with adult human teeth in both enamel and dentin. And the hardness of enamel in the regenerative tooth-like structures formed from embryo stem cell may reaches one-eighth of that in adult human teeth, and the hardness of enamel in the regenerative tooth-like structures formed from iPSC may reach one-forth to one-third of that in adult human teeth.

The tooth-like structures obtained in the examples of present disclosure were confirmed by the physical properties such as elastic modulus and harness by Nano-indentation and constituents by Raman spectroscopy.

It was known that iPSCs (induced pluripotent stem cell) could be efficiently reprogrammed from many cell types, such as keratinobytes, neural stem cells, adipose stem cells, meningiocytes, periosteal membrane, and extraembryonic tissues. And the inventors find interestingly that the kidney contains an extensive network of tubules, whose total surface is bigger than the skin. As part of normal physiology approximately 2000 to 7000 cells from this tubular system and downstream parts of the urinary tract (ureters, bladder, and urethra) detach and are excreted in urine daily. These cells hereafter termed urine cells not only are not damaged but are fully functional and can be used for in vitro studies. Besides, they can be collected anywhere without medical assistance and are easily expanded.

The person skilled in the art may generate human iPSCs from renal tubular cells present in urine (also referred as Human urine cells (hU)) by any known method. For example the person skilled in the art may generate iPSC using retroviral vectors of reprogramming factors Oct4, Sox2, K1f4 and c-Myc. More importantly, the urine-resulting iPSCs display an excellent ability to differentiate, suggesting that urine may be a preferred source for generating iPSCs. And the person skilled in the art may also derive integration-free human urine induced pluripotent stem cells (ifhU-iPSCs) from human urine cells (hU) by oriP/EBNA episomal vectors carrying a combination of reprogramming factors Oct4, Sox2, SV4OLT, K1f4 and miR302/367 through electroporation (Yu, J. et al. Human induced pluripotent stem cells free of vector and transgene sequences. Science 2009:324, 797-801; Liao, B. et al. MicroRNA cluster 302-367 enhances somatic cell reprogramming by accelerating a mesenchymal-to-epithelial transition. The Journal of biological chemistry 2011:286, 17359-17364. Both of articles are incorporated here by reference). Thus, the present invention describes generation of the tooth-like structures from human induced pluripotent stem cells and human embryonic stem cells (hESCs).

Additional aspects and advantages of the embodiments of present disclosure will be given in part in the following descriptions, become apparent in part from the following descriptions, or be learned from the practice of the embodiments of the present disclosure.

BRIEF DESCRIPTION OF THE DRAWINGS

The aforementioned features and advantages of the invention as well as additional features and advantages thereof will be more clearly understood hereinafter as a result of a detailed description of preferred embodiments when taken in conjunction with the drawings, in which.

DETAILED DESCRIPTION OF THE EMBODIMENT

The present disclosure will be described in detail with reference to the following examples. The standard laboratory practices of the inventors are illustrated in the following examples which are used to exemplify the mode of the present invention. The scope of the present invention shall not be construed as being limited to these examples. According to what is disclosed herein and the common level of those skilled in the art, it shall be appreciated that the following examples are only for illustration and may be subjected to various changes, modifications, and alterations without departing from the scope of the present invention. Unless otherwise stated, all the technologies concerned are conventional technologies in embryology, stem cell biology, molecular biology, tissue physiology immunology, histology, engineering, or other fields as well known by those skilled in the art.

General Procedures

Cell Culture:

Human urine cells were cultured in primary medium contains DMEM/Ham's F12 1:1 (Hyclone), 10 wt. % of fetal bovine serum (FBS; PAA), SingleQuot Kit CC-4127 REGM (Lonza), ampothericin B and penicillin/streptomycin for 2 days and then changed to REBM (Renal Epithelial Basal 2 Medium, Lonza) medium containing SingleQuot Kit CC-4127 REGM (Lonza) (referred to as urine cell medium) during the following days. hESCs was purchased from NATIONAL STEM CELL BANK IN USA. iPSCs generated through retroviral vectors or oriP/EBNA episomal vectors (integration-free) were obtained from South Stem Cell Bank in China. Both hESCs and iPSCs were cultured on the Matrigel-coated plates in mTesR1 medium.

Figure 1:
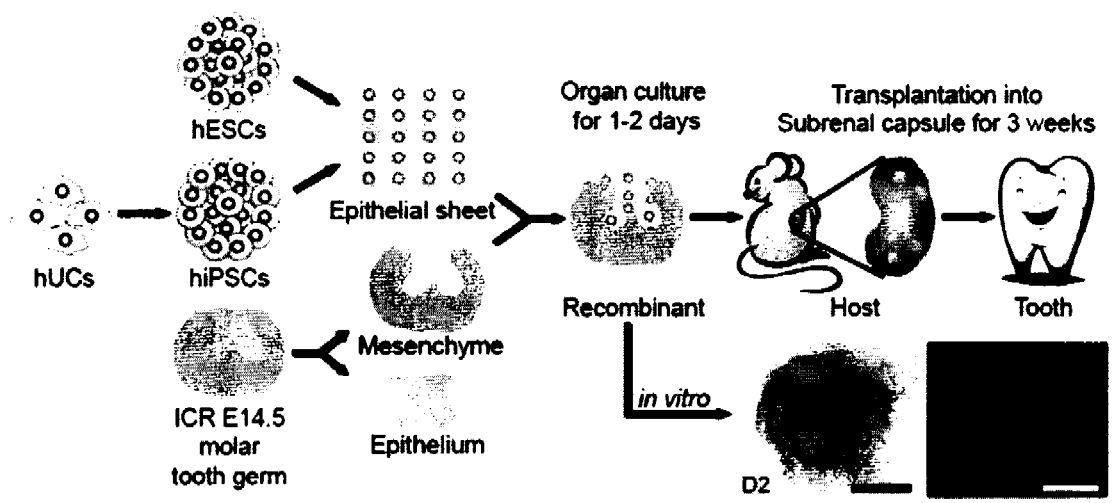
FIG. 1 shows a schematic representation of procedures for tooth generation from hESCs and urine cell derived hiPSCs in one example of present disclosure.

Tooth Generation:

FIG. 1 shows a schematic representation of procedures for tooth generation from hESCs and urine cell derived hiPSCs in one example of present disclosure. A chimeric culture system is developed for tooth regeneration from hESCs and human urine cell derived iPSCs. Briefly, referring to FIG. 1, hESCs or hiPSCs can be induced to produce epithelial sheets capable of replacing the E14.5 mouse dental epithelium in a reconstitution process. The reconstituted explants can then be cultured in vitro for 1-2 days and transplanted beneath mouse subrenal capsule for 3 weeks (≥2 weeks) for tooth regeneration (FIG. 1).

EXAMPLE 1

Production of Epithelial Sheets from hESCs and Integration-Free Human Urine Cell Derived iPSCs (ifhU-iPSCs)

We first devised a way to obtain dental epithelia from hESCs or ifhU-iPSCs and decided on a stage-specific approach based on RA and BMP4 in N2 medium comprising a N2 supplement of about 1 wt. %, a retinoic acid of about 1 μM, and a BMP-4 of about 25 ng/ml. To this end, we obtained epithelial cells with keratinocyte-like morphology at D7 (FIG. 2a). We then allowed the cells to grow as epithelial sheets without passage, and they became denser at D14, and detached slightly with some cell death at D21 (FIG. 2a). The differentiating cells at D7, 14, 21 were harvested and investigated for the expression of pluripotent and keratinocyte progenitor's markers by qPCR and Western blot. During epithelial differentiation, H1-ESCs and ifhU-iPSCs behaved similarly as shown with markers examined at RNA level (Oct4, K18, p63, K19, CD29, and K14), showing upregulated expressions in epithelial markers and downregulation of pluripotent marker Oct4 (FIG. 2b). Similar trends were also observed for protein expression (Oct4, K18 and p63, FIG. 2c). Moreover, the expression of p63 and K14 were verified by immunofluorescence. p63 was detected earlier at D7 and continuously expressed at D21, while K14 expression was detected later at D21 (FIG. 2d). As a result, we obtained homogenous layers of epithelial cells as sheets from both hESCs and ifhU-iPSCs at D7 (FIG. 2d). These sheets harvested at D7 were tenacious and flexible, showing the flat and smooth surface at the apical side as observed by scanning electronic microscopy (SEM) (FIG. 2e). The sheets became rugged with prominent nuclei at D14 (FIG. 2e). Under transmission electron microscopy (TEM), the desmosomes could be observed clearly between the epithelial cells at both D7 and D14 (FIG. 2e). Together, these results suggest that the epithelial sheets generated at D7 from hESC or ifhU-iPSCs have desired properties for being induced for tooth regeneration.

Figure 2:
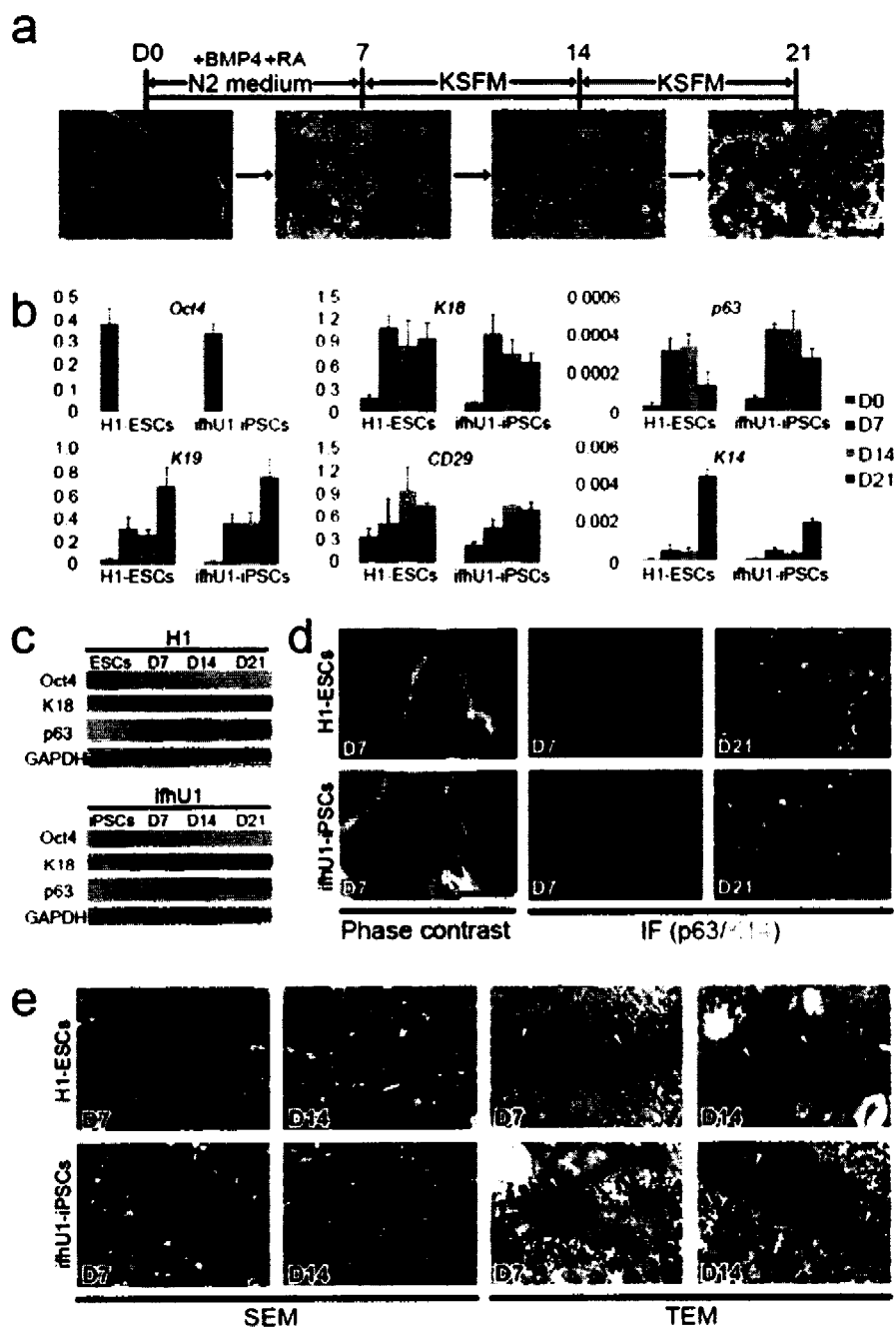
FIG. 2 shows the properties of the hESC/iPSC derived epithelial lineages in one example of present disclosure.

In details, FIG. 2 shows the properties of the hESC/iPSC derived epithelial lineages in one example of present disclosure.

In the FIG. 2, (a) shows the epithelial differentiation process of hESCs or hiPSCs through supplement of RA and BMP4 in N2 medium for 7 days, then changing into DSFM for further differentiation. Scale bar corresponds to 200 μm.

(b) shows qPCR of representative experiment showing the down regulation of ESC-specific transcription factor (Oct4) and up regulation of keratinized epithelial markers (K18, p63, K19, CD29, K14).

(c) shows Western blotting for Oct4, p63, and K18 of lysates from H1 or ifhU1-iPSCs derived epithelial cells; GAPDH is the loading control.

(d) shows Phase contrast captures and immunofluorescence staining [IF: p63 (red), K14 (green), DAPI (blue)] of epithelial sheets derived from H1 and ifhU1-iPSCs at D7 and D21. Scale bars correspond to 2000 and 200 μm, respectively.

(e) shows Scanning electron microscope (SEM) and transmission electron microscopy (TEM) images of H1-ESCs and ifhU1-iPSCs derived epithelial sheets at D7 and D14. White arrowheads indicate desmosomes between epithelial cells of the sheet. Scale bars in SEM and TEM correspond to 20 and 0.5 μm respectively.

EXAMPLE 2

Figure 3:
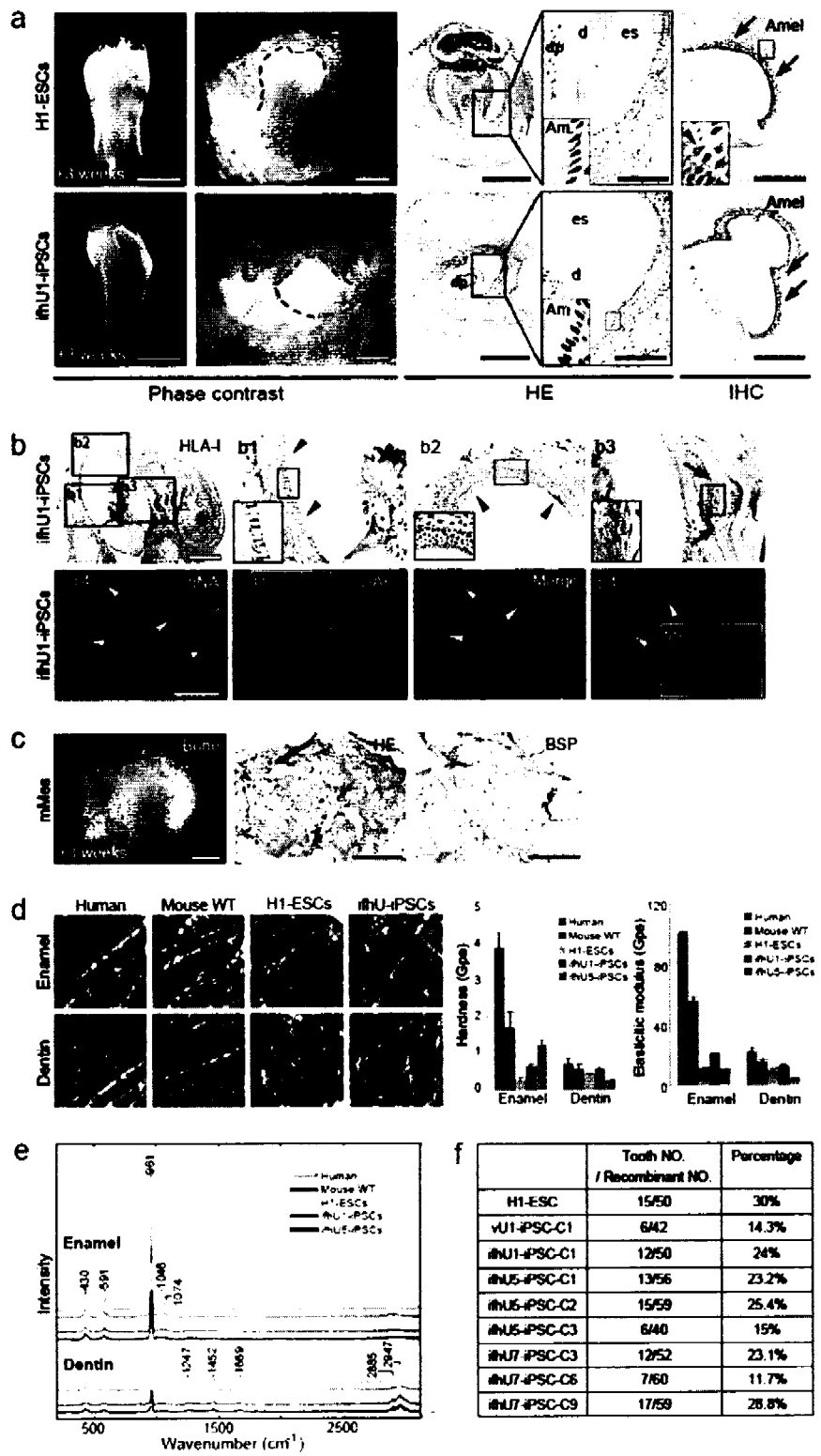
FIG. 3 shows tooth-like structures formed from H1 ESC line and hiPSC lines in 3 weeks in one example of present disclosure.

Generation of Tooth-Like Structure from Epithelial Sheets Derived from hESCs and ifhU-iPSCs We harvested D7 epithelial sheets and recombined them with the mouse dental mesenchyme in a mTeSR1™ medium, E8 medium, or KSR conditioned medium (wherein the medium comprises FBS of about 10 wt. %, glutamine of about 2 mM, non-essential amino acid of about 0.1 mM, penicillin of about 100 U/ml, and streptomycin of 100 U/ml), before transplantation into mouse subrenal capsule (FIG. 1). After 3 weeks, we observed tooth-like structures in the kidney (FIG. 3a). We isolated individual tooth-like structures by removing them from the subrenal capsule and the surrounding bone (FIG. 3a, left columns). The recombinants showed an intact tooth-like structure with dental pulp, dentin, enamel space, and enamel organ (FIG. 3a, middle columns). The enamel organs have elongated ameloblasts with a ruffled border-like structure and papillary layer (FIG. 3a, middle columns). We also observed the expression of Ameloblastin (Amel) located in the layer of ameloblasts and its papillary layer (FIG. 3a). We confirmed the human origin of the epithelial component in cross sections of recombinant tooth prior to isolation by immunostainings with human specific antibodies against human leukocyte antigen-I (HLA-I) and human nucleus antigen (hNA) (FIG. 3b). Both antibodies stained negatively in the dental pulp, cartilage, surrounding bone-like structures, which were developed from mouse dental mesenchyme (FIG. 3b). As expected, both human specific antibodies stained positively for the ameloblasts (FIG. 3b1), papillary layer besides (FIG. 3b2), and squamous epithelial cells in the cyst (FIG. 3b3). Furthermore, positive HLA-I staining was localized in the cytoplasm, while hNA was complementarily localized in the nucleus (FIG. 3b4, b5). As control, without recombination with hESCs or ifhU-iPSCs derived epithelial sheets, mouse dental mesenchymes transplanted under identical conditions formed bone-like structure instead (n=10/10), as confirmed by positive staining of bone sialoprotein (BSP) in the whole bone-like structure embedded with osteocytes (FIG. 3c).

EXAMPLE 3

Characterization of Physical Properties of Tooth-Like Structures and Proportion of Tooth-Like Structure Generation We analyzed the hardness and elastic modulus of human adult teeth (human group), 3-week mouse teeth developed from tooth germs under kidney capsule (Mouse WT group), and the regenerative teeth from H1-ESCs and ifhU-iPSCs groups by Nano-indentation (FIG. 3d). The harness and elastic modulus of dentin and enamel in five groups showed similar properties (FIG. 3d). In the case of enamel, the hardness and elastic modulus of H1-ESCs and two ifhU-iPSCs groups were lower than those of human and Mouse WT groups (FIG. 3d, right graphs). Interestingly, the hardness of ifhU5-iPSCs group was around 4 times higher than that of H1-ESCs group (FIG. 3d, right graphs). Impressively, the hardness of ifhU5-iPSCs group reached ⅓ by comparison with that of human group (FIG. 3d, right graphs). We further analyzed the physical properties of the teeth by Raman spectroscopy. We showed that they all have similar spectra with comparable intensity (FIG. 3e). In the 5 groups examined, the enamel of the teeth are highly mineralized and the spectra showed almost the same spectrum as hydroxyapatite [$Ca_5(PO_4)_3OH$], the primary mineral in teeth] (FIG. 3e). These tooth-like structures also showed similar signs of protein with Raman peaks in dentin, including the hydroxyapatite pick compared to human teeth (FIG. 3e). These results indicated that the regenerative teeth from both H1-ESCs and two ifhU-iPSCs groups have similar constituents with human and mouse teeth. We analyzed a total of 8 hiPSC lines from three urine donors (U1, 5, 7) for tooth regeneration and had a success rate of up to 30% (FIG. 3f).

In details, FIG. 3 shows tooth-like structures formed from H1 ESC line and hiPSC lines in 3 weeks in one example of present disclosure.

In the FIG. 3, (a) Left two columns shows Phase contrast captures of tooth-like structures after and before isolated from the surrounding bone from H1-ESC and ifhU1-iPSC groups (tooth is outlined by a dotted line); right three columns: Hematoxylin-Eosin staining (HE) and immunohistology staining (IHC: Ameloblastin, Amel) of relative tooth sections (H1-ESC: sagittal section; ifhU1-iPSC: cross section), showing the tooth-like structures containing dental pulp (dp), dentin (d), enamel space (es), and a layer of ameloblasts (Am) in both groups. Elongated ameloblasts were showed at the high magnification in the blue box. Positive Amel expression was specifically localized in these ameloblasts with the papillary layer (black arrows). The papillary layer was further pointed out by black arrowheads at the high magnification in the green box. Scale bar: the upper and bottom figures in the same column share the same scale bar as 500, 500, 400, 100, 100 pm from left to right orderly.

(b) shows Immunohistology and immunofluorescence staining in cross sections of the ifhU1-iPSCs derived tooth: top, HLA-I expression was specifically localized in the cytoplasm of human iPSC derived cells and tissues, including ameloblast layer (black arrowheads in b1 and b2) and epithelium-derived cyst (black arrows in b3); bottom, complementary expression of hNA (green) in the nucleus of the same regions in ameloblasts (white arrowheads) and cyst epithelial cells (white arrow). * indicated cyst. DAPI is shown in blue. Higher magnifications of hNA and DAPI in ameloblasts (white arrowheads) were shown in b4 and b5 respectively. Scale bars correspond to 200 µm.

(c) shows Image of a piece of bone detected from E14.5 mouse dental mesenchyme being transplanted under kidney capsule for 3 weeks with positive BSP expression. Scale bars: 1000, 100, 100 µm orderly.

(d) shows Nano-indentation analyses: Left: representative images of fractured enamel and dentin surfaces in adult human tooth group (human), group of 3-week mouse tooth from E14.5 tooth germs (Mouse-WT), regenerative tooth groups from H1-ESCs and ifhU-iPSCs; right: hardness and elastic modulus of enamel and dentin in above groups (each group: n=3).

(e) shows Roman spectroscopy analyses of enamel and dentin from human, mouse, hESCs, and ifhU-iPSCs showed great similarity for all groups on Raman peaks, including 961 $cm^{-1}$ (hydroxyapatite) in both enamel and dentin, and 1669 $cm^{-1}$ (C=O stretching vibration), 2885 $cm^{-1}$ and 2941 $cm^{-1}$(C—H stretching vibration) in dentin.

(f) shows efficiencies of tooth-like structures for H1 ESC line and 8 iPSC lines.

EXAMPLE 4

In this example, human embryo stem cell (H1-ESC) and eight different lines of iPSC derived from urine cells are used to prepare ameloblast respectively in a way similar to the above examples. And the respective efficiency of obtaining ameloblast are compared among these stem cells, the results are shown in the following table I.

TABLE I

| iPSC clone lines | Number of newly formed Teeth/ Number of recombinant specimen | Efficiency in term of percentage |
|---|---|---|
| H1 -ESC | 15/50 | 30% |
| vUC1-iPSC-C1 | 6/42 | 14.3% |
| UC1-iPSC-C1 | 12/50 | 24% |
| UC5-iPSC-C1 | 13/56 | 23.2% |
| UC5-iPSC-C2 | 15/59 | 25.4% |
| UC5-iPSC-C3 | 6/40 | 15% |
| UC7-iPSC-C3 | 12/52 | 23.1% |
| UC7-iPSC-C6 | 7/60 | 11.7% |
| UC7-iPSC-C9 | 17/59 | 28.8% |

In the above table, vUC1-iPSC-C1 represents a iPSC clone line obtained using a retroviral system, and the other 7 lines represent iPSC clone line obtained by means of Electroporation.

As shown by the table I, both human embryo stem cell and iPSC can form a tooth-like structure containg ameloblast, and the efficiency of human embryo stem cell (H1-ESC) may reach 30%, which is higher than that of iPSC. All of the eight lines of iPSC above listed are derived from urine cell, which may have different efficiencies each other. Then we may draw a conclusion that both human embryo stem cell and iPSC can be used to prepare ameloblast with a relative higher efficiency.

Although explanatory embodiments have been shown and described, it would be appreciated by those skilled in the art that changes, alternatives, and modifications all falling into the scope of the claims and their equivalents can be made in the embodiments without departing from spirit and principles of the disclosure.

What is claimed is:

1. A method of preparing a tooth-like structure, wherein said tooth-like structure is prepared from a human induced pluripotent stem cell, and wherein said human induced pluripotent stem cell is prepared from a stem cell derived from a urine cell.

2. The method of claim 1, wherein the tooth-like structure is produced in a mammalian animal by means of xenograft transplantation.

3. The method of claim 2, wherein the mammalian animal is at least one selected from a group consisting of mouse, rat, pig, dog, and monkey.

4. The method of claim 1, wherein the stem cell is induced to form an epithelial-like cell prior to the xenograft transplantation.

5. The method of claim 1, wherein the tooth-like structure comprises an ameloblast.

6. A method for preparing an ameloblast, comprising:
preparing an epithelial-like cell by a method comprising culturing a stem cell using a first culture medium comprising a DMEM/F12 medium supplemented with about 1 wt. % N2 supplement, about 1 µM retinoic acid and about 25 ng/ml BMP-4, to induce the stem cell differentiating into the epithelial-like cell;
preparing a dental mesenchyme from a first animal;
recombining the epithelial-like cell with the dental mesenchyme to obtain a recombinant specimen;
culturing the resulting recombinant specimen to obtain a reconstituted explant; and
transplanting the reconstituted explant into a second animal for at a predetermined time to form the ameloblast, wherein the stem cell is an induced pluripotent stem cell derived from a urine cell.

7. The method of claim 6, wherein the stem cell is cultured for about 5-10 days.

8. The method of claim 6, wherein the first animal and the second animal are independently selected from a group consisting of mouse, rat, pig, dog, and monkey respectively.

9. The method of claim 7, wherein the first animal is a fetal mouse, and the second animal is a nude mouse.

10. The method of claim 9, wherein the dental mesenchyme is mechanically separated from a tooth germ, and the tooth germ is digested using a protease prior to the separation.

11. The method of claim 10, wherein the protease is a Dispase of about 0.75 mg/ml.

12. The method of claim 6, wherein the resulting recombinant specimen is cultured using a DMEM medium supplemented with FBS, non-essential amino acid, glutamine, penicillin and streptomycin.

13. The method of claim 9, wherein the recombinant tissue is transplanted into a space under a kidney capsule of the nude mouse.

14. The method of claim 6, wherein the predetermined time is about 2 to 4 weeks.

15. The method of claim 6, wherein the predetermined time is about 3 weeks.

16. The method of claim 6, wherein the stem cell is cultured using at least one medium selected from the group consisting of mTeSR1 medium, E8 medium, and KSR-conditioned medium prior to preparing the epithelial-like cell,
wherein the medium is replaced with the first culture medium when the cultured stem cell reach a confluence of about 60-80%, to obtain the epithelial-like cell, said first culture medium being DMEM/F12 medium supplemented with a N2 supplement of about 1 wt. %, a retinoic acid of about 1 μM, and a BMP-4 of about 25 ng/ml.

* * * * *